United States Patent [19]

Fort

[11] Patent Number: 5,278,639
[45] Date of Patent: Jan. 11, 1994

[54] COLOR FILTER WHEEL FOR ENDOSCOPES AND PROCESSING OF GENERATED COLOR

[75] Inventor: Francois Fort, Paris, France

[73] Assignee: Fort Fibres Optiques Recherche Et Technologie, Dourdan, France

[21] Appl. No.: 910,370

[22] PCT Filed: Dec. 13, 1991

[86] PCT No.: PCT/FR91/01006

§ 371 Date: Aug. 13, 1992

§ 102(e) Date: Aug. 13, 1992

[87] PCT Pub. No.: WO92/10907

PCT Pub. Date: Jun. 25, 1992

[30] Foreign Application Priority Data

Dec. 13, 1990 [FR] France ............... 90 15608

[51] Int. Cl.⁵ ......................................... H04N 5/225
[52] U.S. Cl. ........................................ 358/42; 358/98
[58] Field of Search ............ 358/42, 98; H01N 5/225

[56] References Cited

U.S. PATENT DOCUMENTS

| | | | |
|---|---|---|---|
| 3,529,080 | 9/1970 | Nassimbene | 358/42 X |
| 4,329,709 | 5/1982 | Masuda et al. | |
| 4,593,313 | 6/1956 | Nagasaki et al. | 368/42 X |
| 4,621,284 | 11/1986 | Nishioka et al. | 358/98 |
| 4,774,565 | 9/1988 | Freeman | |
| 4,914,512 | 4/1990 | Sekiguchi | 358/98 |
| 4,998,973 | 3/1991 | Kikuchi | |
| 5,045,934 | 9/1991 | Kikuchi | 358/98 |
| 5,046,162 | 9/1991 | Ishikawa et al. | 358/42 |
| 5,111,281 | 5/1992 | Sekiguchi | 358/98 X |

OTHER PUBLICATIONS

Patent Abstracts of Japna, vol. 8, No. 17 (E-223) (1454) Jan. 25, 1984 & JP, A, 58 179 083 (Nippon Denki K.K.) Oct. 20, 1983.
Patent Abstracts of Japan, vol. 12, No. 395 (E-671) Oct. 20, 1988 & JP, A,63 136 787 (Olympus Optical Co., Ltd.) Jun. 8, 1988.
Patent Abstract of Japan, JP,A,63 311 937 (Toshida Corp) Dec. 20, 1988.
Patent Abstracts of Japan, vol. 13, No. 12 (P-812) Jan. 12, 1989 & JP,A,63 220 215 (Olympus Optical co. Ltd.) Sep. 13, 1988.

*Primary Examiner*—Mark R. Powell
*Attorney, Agent, or Firm*—Bell, Seltzer, Park & Gibson

[57] ABSTRACT

The color video-endoscope (100) comprises in particular:
- a single light source (10);
- a bundle of optical fibers (40) for transmitting the light to a field of observation;
- a periodic filtering device (50) including three filters (53, 54, 55) illuminating the field of observation with three respective primary colors (R, G, B), and a fourth filter zone (56) which is transparent and through which the light also passes;
- a photosensitive sensor (60) for picking up an image of objects situated in the field of observation;
- an analog-to-digital converter (91) for digitizing the periodic information from the sensor (60) representative of color images (RGB) and of a black-and-white image (B/W), with the digital information being stored in four respective memories (81 to 84); and
- a color toning device (85a, 85b) selectively combining the black-and-white image information (B/W) with the color information for the purpose of reconstituting a color image of very good quality.

2 Claims, 2 Drawing Sheets

COLOR FILTER WHEEL FOR ENDOSCOPES AND PROCESSING OF GENERATED COLOR

BACKGROUND OF THE INVENTION

The present invention relates to a method of sensing and processing images for a color video-endoscope, and to a video-endoscope implementing the method.

Patent FR-2 438 999 describes an endoscope for processing color information and for forming a read signal, in particular a signal compatible with a television set (a priori any television set of standardized format), i.e. for making color images of a field of observation (namely of objects situated in said field).

That French patent uses a lighting system based on the teaching of the U.S. Pat. No. 4,074,306 in which information about the image observed in the field scanned by the observation head of the endoscope is split into three primary colors, in particular Red, Green, and Blue (RGB). The original color image is then recreated by combining partial images in each of these three primary colors RGB. The three RGB images are formed by mechanically filtering the light used to illuminate the cavity being explored (by means of the observation head of the endoscope) by using a single light source associated with a rotary disk for providing RGB filtering of the light it provides. In a variant, the three RGB images may also be formed by splitting an image reflected from the field of observation by means of a series of dichroic mirrors.

French patent FR-2 438 999 thus differs from American U.S. Pat. No. 4,074,306 essentially in that the three separated light images, each containing data corresponding to an individual one of the primary colors RGB, are created by successively controlling a series of lamps that have short response times.

In addition, that French patent makes use of an individual light source for each of the primary colors (RGB) used in the video system adopted, which light is transmitted to the field of observation being explored by the head of the endoscope via a bundle of optical fibers. Furthermore, each of the primary color (RGB) images is formed in succession on a semiconductor image-forming device, and the output signals therefrom are coupled electrically to a memory for storing each of the read color signals individually, the color signals stored in the above memory being periodically applied to an image processing circuit for making the corresponding information available in a for-mat that is compatible with the format of a color receiver.

Nevertheless, the image of the observed field as reconstituted by analog means in this way does not have the brightness and contrast that is desirable in this kind of application, where it is essential to show up clearly the details of the field of observation that contain important optical information.

An object of the present invention is to eliminate the drawbacks of the prior art in such a manner as to obtain color images of the observed field having brightness and contrast that are better than those obtained in the prior art, with this having the additional advantage of an increase of at least 30% in the observation distance (between the read head of the video-endoscope and the field of observation).

SUMMARY OF THE INVENTION

To this end, the present invention provides a color video-endoscope for providing color information concerning a field of observation in a cavity to be explored, said information being in a form such as to enable it to be displayed on a standard format video receiver, for example, the video-endoscope comprising:

- a single lighting source;
- a bundle of optical fibers for conveying light from said source to the field of observation;
- a periodic filtering device for filtering the light emitted by the above-mentioned source, and including first, second, and third filter zones enabling the field of observation to be periodically illuminated via the above-mentioned bundle with three primary colors (RGB) respectively corresponding to light passing through each of the three above-mentioned filter zones, and a fourth filter zone which is transparent and through which the light also passes;
- a photosensitive sensor designed to pick up an image of objects situated in the field of observation illuminated through the filter device;
- an analog-to-digital converter for digitizing the periodic information from the sensor and representative of color images (R, G, B) and a black-and-white image (B/W), with the digital information being stored in four memories corresponding respectively to the color information (R, G, B) and to the black-and-white information (B/W);
- a color toning device for selectively combining the black-and-white image information (B/W) with the color information;
- a digital-to-analog converter for converting the digital signals output by the toning device into analog form; and
- an encoder forming an interface with a display apparatus for reconstituting a color image.

According to another characteristic of the invention, the color video-endoscope includes a switching device for controlling the storage of the information sent by the sensor and converted by the converter synchronously with rotation of the filtering device.

In general, the color toning device comprises adder circuits and may also comprise subtractor circuits, which operations are advantageously weighted operations.

In an embodiment, the color toning device comprises three adder circuits for adding together respectively the green and blue color signals stored in the memories, the red and blue color signals stored in the memories, and the red and green color signals stored in the memories, and in that it includes three subtractor circuits having their inputs connected to respective ones of the three adder circuits and to the memory in which the black-and-white signals are stored, with the outputs from the subtractor circuits being connected to the digital-to-analog converter means.

In a second embodiment, the color toning device comprises three adder circuits for adding the black-and-white signals stored in the memory with each of the respective color signals stored in the memories.

The invention also provides a method of sensing and processing color images by means of a video-endoscope as defined by any preceding claim, the method comprising the following steps:

- illuminating a field of observation by means of a light source and a bundle of optical fibers for transmitting light;

periodically filtering the light emitted by the source using three filter zones to illuminate the field of observation with three primary colors (R, G, B), and a fourth filter zone that is transparent and allows the light to pass;

using a photosensitive sensor to periodically sense the images reflected by the field of observation and corresponding respectively to red, green, and blue color images and to a black-and-white image;

converting the information picked up by the sensor into digital form and storing it in four memories corresponding to the red, green, and blue color image signals and to the black-and-white image signals; and selectively processing the signals stored in the memories on the basis of the black-and-white signals to tone the colors of an image reconstituted from the signals processed in this way.

According to another characteristic of the invention, the method consists in processing the signals stored in the memory by performing addition operations, and it consists in particular in adding the black-and-white signals to the red, green, and blue signals respectively, and in combining the signals added together in this way to reconstitute a color image, with the addition operations advantageously being weighted operations.

It is thus possible to obtain better image quality in particular better sensitivity because of the additional formation as contained in the black-and-white image.

BRIEF DESCRIPTION OF THE DRAWINGS

The invention will be better understood in the light of the following description made with reference to the accompanying drawings, in which.

DETAILED DESCRIPTION

Figure 1:
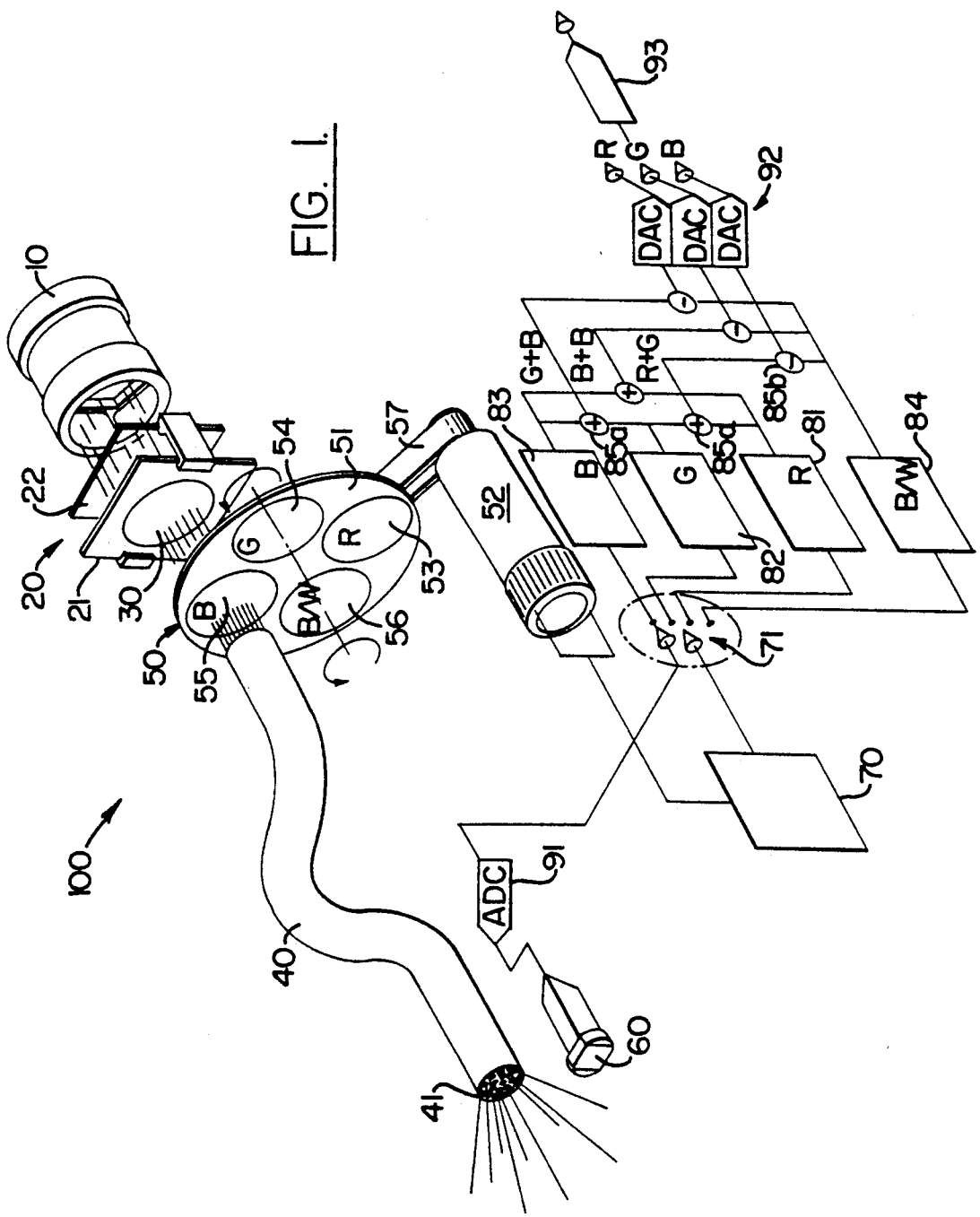
FIG. 1 is a diagram showing the principle on which a video-endoscope of the invention operates.

Numerical reference 10 designates an arc lamp of the star type disposed at the center of a radiator (not shown) and designed to cooperate with a fan (also not shown) that generates a forced cooling draft for the lamp (which has a power of about 300 W in the embodiment shown). Given that the electric arc is struck using a very high voltage (about 5000 V), it is necessary to provide appropriate measures for safety in use, as is known to the person skilled in the art.

An anti-heat device 20 follows the lamp 10. This device includes two anti-heat filters 21 and 22 which are spaced apart in appropriate manner and which serve to provide the necessary thermal protection by eliminating the infrared radiation (IR) in the light emitted by the lamp 10.

A diaphragm (not shown) is generally used to adjust the intensity of the light under electronic control using dispositions known to persons skilled in the art.

A condenser lens 30 serves to focus the light beam from the lamp 10 onto the axis of a bundle of optical fibers 40.

A device 50 for filtering the light emitted by the lamp 10 is disposed between the anti-heat device 20 and the bundle 40.

This filter device comprises a disk 51 rotated by a motor 52 (with transmission being provided by means of a toothed belt 57), and it includes four filter zones.

Three of the filter zones 53, 54, and 55 (which are conventional in this type of device) are intended to illuminate the field of observation (not shown) inside a cavity to be explored periodically with the three primary or fundamental colors, namely Red, Green, and Blue (RGB) respectively. The fourth zone 56 is transparent, i.e. it allows the light emitted by the lamp 10 to pass unaltered (i.e. without being filtered).

This is the same as saying that the filter disk 51 is subdivided into four quandrants, each of which is occupied by a respective one of the above-mentioned zones 53 to 56. More precisely, in the embodiments described herein, the opaque zones of the rotary disks 51 are defined by sectors of about 35°, whereas the filter zones 53 to 55 and the transparent zone 56 are defined by sectors of about 55°, with the above filter zones being constituted by respective RGB filters of type known to persons skilled in the art.

Naturally, a "shadow" zone exists between any two adjacent zones, i.e. a zone which is opaque to the light emitted by the source 10. It is during the time required by the rotary disk 51 to pass from one zone to the next zone that processing takes place of the optical information in each of the three primary colors corresponding to the field of observation being illuminated with RGB, or with W (i.e. white light W, that is to say without filtering). The RGB and black-and-white (B/W) images of the field of observation as obtained in this way are picked up by a photosensitive sensor 60 which is preferably constituted by a semiconductor device such as a CCD camera, and which is disposed adjacent to the distal end 41 of the bundle of optical fibers 40 in the above-mentioned observation head of the video-endoscope 100 (in practice, the fibers of the bundles 40 are disposed in a crescent moon shape in the observation head of the video-endoscope, with the remainder of the circular zone occupied by the observation head being occupied by the CCD camera).

The observation head is advantageously of the type constituted by mutually articulated rings and suitable for being controlled by a cable by means of a control handle, which dispositions are known to persons skilled in the art.

The optical and electrical cables are preferably combined in a single Y-shaped cable.

The optical information picked up by the CCD camera is converted into digital form by an analog-to-digital converter 91 and the digital information is then stored in four memories 81 to 84 corresponding respectively to the black-and-white signals. This digital information is stored via a switching device 71 controlled by a control device 70 which ensures that the storage operation is synchronized with the operation of the filtering performed by the rotating filter disk 51.

The signals recorded in the memories 81 to 84 are then processed selectively, given that the signals corresponding to the black-and-white image B/W contain additional information, particularly with respect to sensitivity, compared with the information contained in the signals corresponding to the red, green, and blue color signals. Combinations are thus made of the signals on the basis of the signals stored in the memories 81 to 84, e.g. by using processing circuits which perform addition and subtraction operations. Together these circuits constitute a "color toning" device for the purpose of reconstituting a final color image whose quality is considerably improved over that of an image reconstituted solely by combining three color images.

In a first embodiment of this toning device, as shown in FIG. 1, the signals representing the green color image as stored in the memory 82, whose amplitudes constitute to the brightness G of the green color are combined with the signals representing the blue color image as stored in the memory 83, whose amplitude correspond to the brightness of the blue color B. These signals are combined in a processing circuit 85a which overall performs an addition operation, and the amplitude of the signals then corresponds to the brightness of the original image minus the brightness R of the red color image. Thereafter, the signals combined by the processing circuit 85a and the black-and-white signals stored in the memory 84 are processed by a processing circuit 85b which overall performs a subtraction operation, thereby defining output signals whose amplitude corresponds to brightness R of a red color image which is improved relative to the original red color image.

The same procedure is applied by combining the signals representing the blue and red color images in a processing circuit 85a and by combining the resulting signals with the black-and-white signals in a processing circuit 85b to obtain output signals of amplitude corresponding to the brightness G in a green color image that is improved relative to the original green color image. Finally, the signals of the red and green color images are combined in a processing circuit 85a, and the resulting signals are combined with the black-and-white signals in a processing circuit 85b, thereby obtaining output signals of amplitude corresponding to the brightness B of a blue color image that is improved relative to the original blue color image.

The output signals from the processing circuits 85b are then converted into analog signals by a digital-to-analog converter 92 and a color image is reconstituted by an encoder 93 compatible with a standardized format television set, for example one selected from video standards such as NTSC, PAL, or SECAM.

Figure 2:
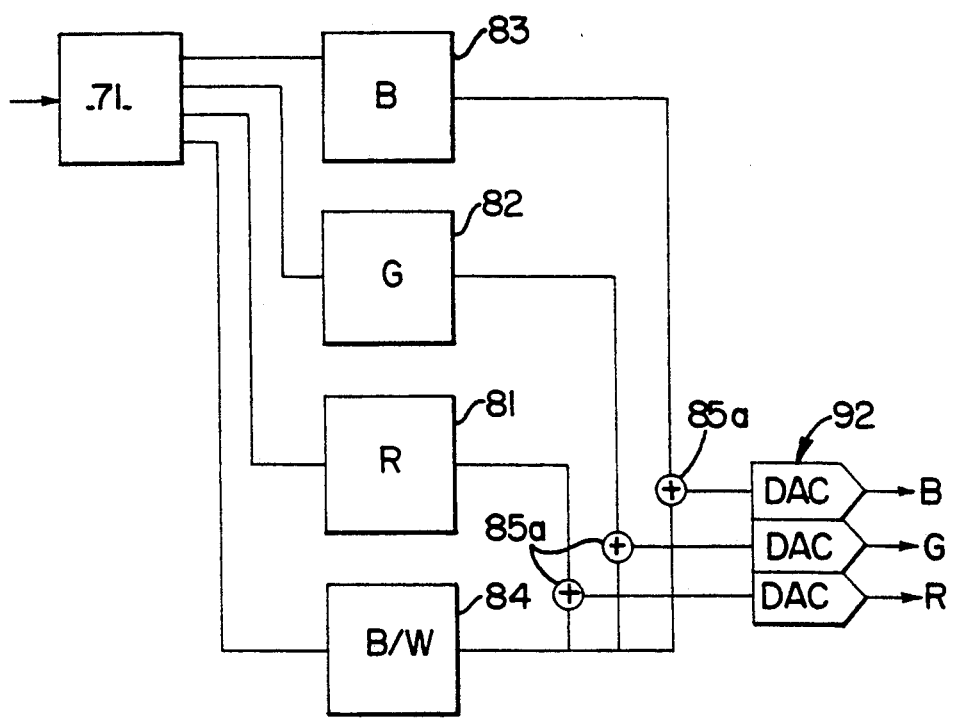
FIG. 2 is a block diagram showing a variant of the processing circuits used for reconstituting a color image.

In a variant, as shown in FIG. 2, the signals stored in the memories 81 to 84 may be processed by combining the black-and-white signals stored in the memory 84 in three processing circuits 85a of the above-mentioned type with respective ones of the signals stored in the memories 81 to 83. The outputs from these three processing circuits 85a provides signals corresponding to three black-and-white images respectively colored red, green, and blue, each of which images has improved quality over the corresponding original red, green, or blue color image. Thereafter, the color image is reconstituted from the signal of these three images by means of the digital-to-analog converter 92 and the encoder 93, as before.

Advantageously, the processing circuits 85a and 85b may be associated with weighting functions for acting on the brightnesses of the colors red, green, and blue, thereby modifying the colors in the reconstituted image for the purpose of improving the quality thereof.

Naturally the video-endoscope of the invention may be used for industrial applications as well as medical applications.

Thus, as can be seen from the above, the invention is not limited in any way to those embodiments and applications described above in greater detail. On the contrary, the invention extends to any variant that may occur to the person skilled in the art without going beyond the ambit or the scope of the present invention.

What is claimed is:

1. A color video-endoscope for providing color information concerning a field of observation in a cavity to be explored, said information being in a form such as to enable it to be displayed on a standard format video receiver, the video-endoscope comprising:

a single lighting source;

a bundle of optical fibers for conveying light from said source to the field of observation;

a periodic filtering device for filtering the light emitted by said source, and including first, second, and third filter zones enabling the field of observation to be periodically illuminated via said optical fiber bundle with three primary colors (RGB) respectively corresponding to light passing through each of the three filter zones, and a fourth filter zone which is transparent and through which the light also passes;

a photosensitive sensor designed to pick up an image of objects situated in the field of observation illuminated through the filter device;

an analog-to-digital converter for digitizing the periodic information from the sensor and representative of color image (R, G, B) and a black and white image (B/W), with the digital information being stored in four memories corresponding respectively to the color information (R, G, B) and to the black and white information (B/W);

a color toning device for selectively combining the black-and-white image formation (B/W) with the color information, said color toning device comprising three adder circuits for adding together respectively the green and blue color signals stored in the memories, the red and blue color signals stored in the memories, and the red and green color signals stored in the memories, three subtractor circuits having their inputs connected to respective ones of said three adder circuits and to the memory in which the black and white signals are stored;

a digital-to-analog converter connected to the outputs from said subtractor circuits and operable for converting the digital signals output by the toning device into analog form; and an encoder forming an interface with a display apparatus for reconstituting a color image.

2. A color video-endoscope according to claim 1, additionally including a switching device for controlling the storage of the information sent by the sensor and converted by the converter synchronously with rotation of the filtering device.

* * * * *